United States Patent [19]

Hauer

[11] Patent Number: 5,417,657
[45] Date of Patent: May 23, 1995

[54] NO-SEPSIS URINARY DRAINAGE CATHETER

[76] Inventor: Carolyn Hauer, 452 Kirk Rd., Palm Springs, Fla. 33461

[21] Appl. No.: 132,719

[22] Filed: Oct. 6, 1993

[51] Int. Cl.⁶ ........................................... A61M 29/00
[52] U.S. Cl. ........................................ 604/96; 604/43; 604/100; 604/101; 604/102; 604/104; 604/256; 604/280; 606/192
[58] Field of Search ............... 604/43, 96, 100, 101, 604/102, 104, 74, 265, 280, 890.1; 606/192

[56] References Cited

U.S. PATENT DOCUMENTS

| | | | |
|---|---|---|---|
| 3,373,735 | 3/1968 | Gallagher | 604/280 |
| 3,394,705 | 7/1968 | Abramson | 604/96 |
| 3,566,874 | 3/1971 | Shepherd et al. | 604/265 |
| 3,981,299 | 9/1976 | Murray | 604/43 |
| 4,211,233 | 7/1980 | Lin | 604/43 |
| 4,423,725 | 1/1984 | Baran et al. | 604/101 |
| 4,579,554 | 4/1986 | Glassman | 604/96 |
| 4,623,329 | 11/1986 | Drobish et al. | 604/265 |
| 4,642,104 | 2/1987 | Sakamoto et al. | |
| 4,946,449 | 8/1990 | Davis, Jr. | |
| 5,007,897 | 4/1992 | Kalb et al. | |
| 5,090,959 | 2/1992 | Samson et al. | |
| 5,098,379 | 3/1992 | Conway et al. | |
| 5,265,755 | 12/1993 | Bodicky | 604/96 |

FOREIGN PATENT DOCUMENTS

2135194 8/1984 United Kingdom ................ 604/102

Primary Examiner—C. Fred Rosenbaum
Assistant Examiner—Bryan L. Tsosie
Attorney, Agent, or Firm—Malin, Haley, DiMaggio & Crosby

[57] ABSTRACT

A no-sepsis urinary catheter, comprising three lumens, each in fluid communication with a drainage tip for receiving urine from the bladder, a retention balloon for retaining the catheter within the bladder, and a microporous bacteriostasis balloon for the diffusion by osmosis of a pharmaceutical agent for the killing and prevention of bacteria growth within and around the bladder to preclude the development of sepsis therein.

18 Claims, 5 Drawing Sheets

NO-SEPSIS URINARY DRAINAGE CATHETER

BACKGROUND OF THE INVENTION

1. Field of the Invention

This invention relates generally to a no-sepsis urinary drainage catheter, and more particularly, to a urinary drainage catheter having a drug delivery system comprising a microporous bacteriostatic barrier that diffuses a bacteriostatic fluid into the bladder by osmosis to effectively reduce the risk of sepsis in the bladder caused by the conventional Foley catheter.

2. Description of the Background Art

A urinary drainage catheter, such as the Foley catheter, is a hollow, tubular device commonly used in the medical profession for insertion into a patient's bladder via the urethral tract to permit the drainage of urine. Use of a urinary catheter is necessary for patients that are undergoing surgery, orthopedically incapacitated, incontinent, or incapable of voluntary urination. An unfortunate problem with catheterization, however, is the development of sepsis as a result of bacterial invasion in the bladder and urinary tract by pyrogenic organisms. Sepsis is potentially lethal and most prevalent in the elderly, where urinary tract and bladder infections become systemic very easily, especially if hygiene is poor and hydration of tissue is deficient. The risk of sepsis increases with the employment of urinary drainage catheters, wherein norma flora bacteria from feces or skin easily ascend into the bladder around the inserted catheter. In addition, residual urine in stasis around the retention balloon provide a culture medium at warm body temperatures that facilitate the growth of bacteria. Consequently, the bacteria is able to accumulate, multiply and become pathogenic in the bladder, eventually circulating into the kidneys and throughout the system, resulting in sepsis of the system. Because of this propensity to produce infection in the patient, medical practitioners often refuse to extend the use of catheters, despite their usefulness. Accordingly, physicians are plagued by the risk associated with catheter use, but they have yet to see a breakthrough.

Although attempts have been made to improve the catheter design, these efforts have been geared towards increasing patient comfort and finding new applications, such as treating prostrate diseases. For instance, a catheter having a lubricated outer sleeve, as disclosed by Conway in U.S. Pat. No. 5,098,379, utilizes a catheter having a single lumen enclosed by a sleeve which together form an elongated lubricated cavity therebetween such that the sleeve may slide along the outer surface of the lumen to move independently with respect to the lumen. This independent movement of the sleeve relative to the lumen represents the object of the invention wherein it is intended to prevent irritation and chafing of tissue in the body portion passageways when a patient moves.

A drug delivery catheter, disclosed by Kalb in U.S. Pat. No. 5,007,897, incorporates a three lumen catheter for draining fluid from the bladder and treating the prostrate gland. The Kalb catheter incorporates a porous membrane which lies adjacent the prostatic ducts so that medication may be transmitted along the lumen into a space between the catheter and a porous membrane for treatment of the prostrate. A path, however, is still created upon chamber insertion allowing the ascension of bacteria into and around the bladder. Thus, Kalb teaches a catheter that treats the male prostrate but continues to carry with it the risk of sepsis found with conventional catheters.

Accordingly, a need exists for a catheter that is not only insusceptible to sepsis causing side affects but that prevents and treats the same in both males and females. The instant invention is intended to address those problems left unresolved by the prior art by providing a no-sepsis urinary drainage catheter which is easily adaptable to the current medical field.

SUMMARY OF THE INVENTION

It is an object of the present invention to provide a no-sepsis urinary drainage catheter having a permeable bacteriostasis barrier that contains a bacteria fighting time release gel delivered around the urethra and bladder floor to prevent the development of sepsis in the bladder by blocking passage thereto and by killing or preventing the growth of bacteria.

It is an additional object of the instant invention to provide a no-sepsis urinary drainage catheter having an acid-base sensitive strip for determining the time for reloading the bacteriostatic barrier.

It is another object of the instant invention to provide a no-sepsis urinary drainage catheter that is more comfortable for the patient and that necessitates less frequent removal and reinsertion, procedures which jeopardize a patient vulnerable to infection.

It is a further object of the instant invention to provide a no-sepsis urinary drainage catheter that would save lives lost from the lethal effects of sepsis, improve the quality of life for the infirm and the elderly, and prevent secondary complications to people already compromised by a diminished immune system, surgery, immobility or incontinence. It is still another object of the instant invention to provide a no-sepsis urinary drainage catheter that is easily adaptable to current medical practice.

It is still an additional object of the instant invention to provide a no-sepsis urinary drainage catheter that is simple in design and structure, and potentially low in cost.

These and other objects are achieved by the present invention which contemplates a no-sepsis urinary drainage catheter for the effective use by both sexes. The device of the present invention generally comprises three lumens, a bacteriostasis barrier and a retention balloon. The no-sepsis catheter is an elongated flexible tube fabricated from either synthetic rubber, latex or similar polymer which maintains a proximal end and a distal end. The proximal end is inserted into the bladder via the urethra while the distal end pends outside the body. In the preferred embodiment, the catheter defines three lumens connecting the proximal and distal ends.

Preferably, the three lumens comprise a drainage lumen, a retention lumen and a barrier lumen. The drainage lumen is typical to the urinary catheter found in the Foley design. The drainage lumen provides fluid communication between a drainage tip at the proximal end and a drainage bag at the distal end to fill the bag with fluid from the bladder.

The retention lumen comprises tubing having a retention inlet near the distal end for fluidly communicating with a nonporous flexible bag, i.e. a retention balloon, disposed below the drainage tip at the proximal end, that is water inflated. When the catheter is inserted into the bladder, the retention balloon is inflated to afford support therein. A pre-filled syringe, pump, plunge, cylinder or similar apparatus may typically be fitted to the retention inlet via a Luer loc valve to inject fluid into the lumen for inflating the retention balloon, or to aspirate the same for deflating the balloon.

The barrier lumen fluidly communicates with a bacteriostatic barrier which together comprise a novel aspect of the instant invention. The bacteriostatic barrier comprises a bladder floor conforming balloon fabricated from a flexible micropore density material, such as a permeable or semi-permeable membrane, to allow the diffusion by osmosis of a timed release pharmaceutical agent from the balloon into and around the bladder. The bacteriostatic balloon is located below the retention balloon and is connected in fluid communication by the barrier lumen with a barrier inlet near the distal end of the catheter. An injection device as aforementioned is generally connected to the barrier inlet via a Luer loc valve for inflating the bacteriostasis balloon with a bacteriostatic infection preventing or treatment solution, such as a bactericide or similar antibody, for killing or inhibiting the growth of bacteria near and in the bladder. Preferably, a timed released bacteriostatic jell or fluid of a neosporin type, an antibiotic, bacterin or similar pharmaceutical agent should be used but in no way should be limited to the foregoing. Additionally, the bacteriostatic gel may contain alkaline aloe vera gel to reduce tissue irritation that can occur upon contact with the skin. Furthermore, the novel no-sepsis catheter includes a refill indicator to warn the cognizant physician, nurse or caretaker when the bacteriostasis balloon requires reloading. The indicator generally comprises an acid-base sensitive strip, such as litmus paper or a litmus coating, extending along the catheter from the bacteriostatic balloon to the distal end which changes color from its base pH induced signal to the acid pH induced color when coming in contact with urine. The gel provides a base or alkaline pH to give the acid base sensitive strip a loaded reading. Some urine diffuses into the barrier balloon by osmosis and changes the color of the litmus strip once the balloon has been sufficiently depleted.

The novel catheter disclosed herein also includes a coating on its outer surface to provide additional comfort and therefore less irritation when it is inserted into and maintained within the urethra. In the preferred embodiment, a colloid material is impregnated on the exterior surface of the catheter shaft as a surfactant providing a comfortable insulation with its spongy, elastic characteristics that also prevent sepsis. Moreover, bladder spasms are mitigated or even prevented because of the comfortable fit through the urethra sphincter.

DESCRIPTION OF THE PREFERRED EMBODIMENTS

With reference to the drawings, FIGS. 1-10 depict a no-sepsis catheter generally indicated by the referenced numeral 10, comprising a drainage lumen 16, a retention balloon 24, a retention lumen 26, a bacteriostasis barrier 32 and a barrier lumen 36. The drainage lumen 16, the retention lumen 26, and the barrier lumen 36 are defined by the catheter 10 which extends longitudinally as a shaft from a proximal end 12 to a distal end 14. The three lumens 16, 26, and 36 provide fluid communication between the proximal end 12 and the distal end 14. The proximal end 12 has a drainage tip 18 which is inserted through the urethra into the bladder of a person. Meanwhile, the distal end 14 pends outside the body where the drainage lumen 16, the retention lumen 26 and the barrier lumen 36 trifurcate into three distinct sections. The drainage tip 18 fluidly communicates with the drainage lumen 16 for draining the bladder near the distal end 14. The retention lumen 26 is in fluid communication with retention balloon 24 for inflating the same, while the barrier lumen 36 provides a passageway to the bacteriostasis barrier 32.

Figures 1, 2:
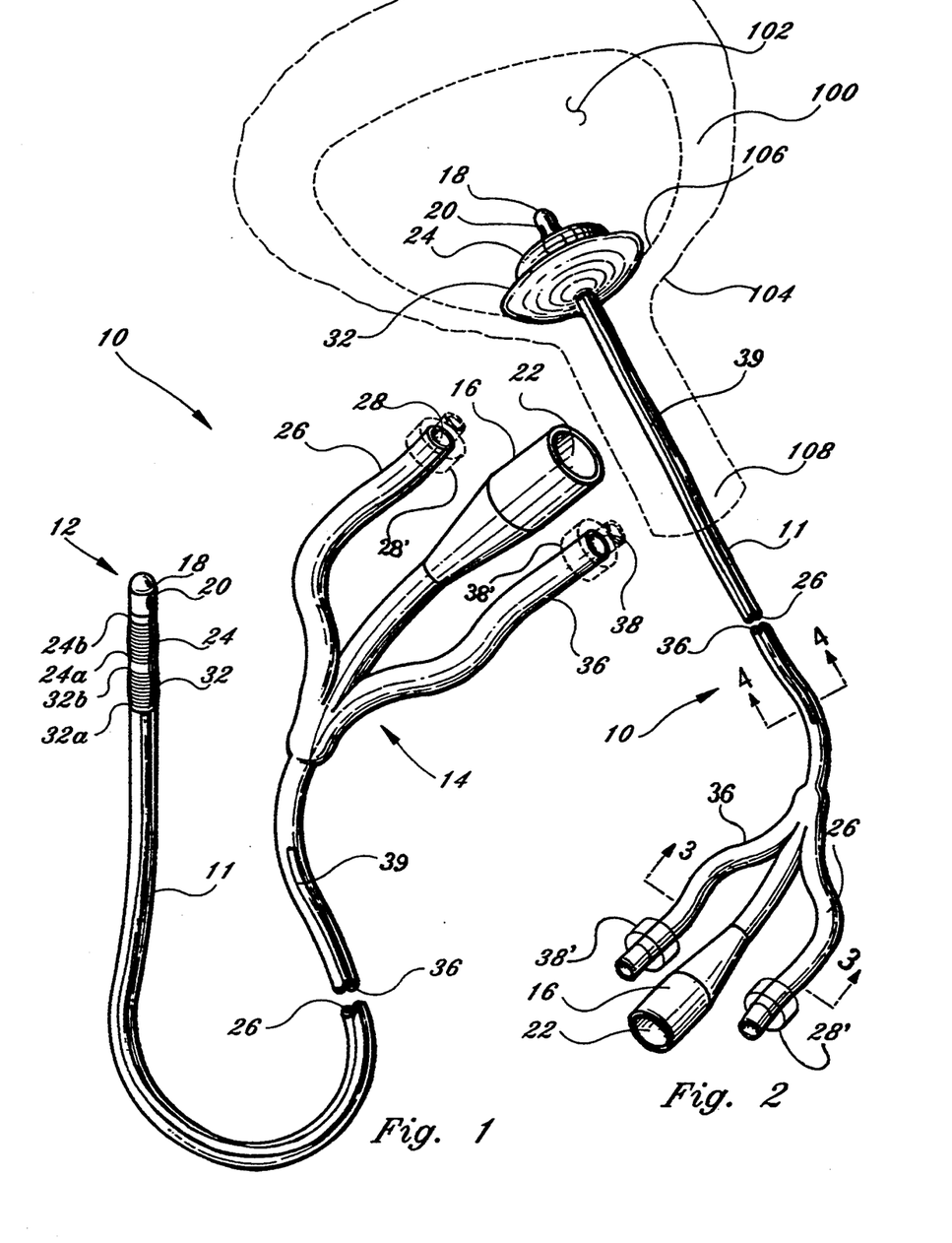
FIG. 1 is a perspective breakaway view of the instant invention, illustrating the balloons in the deflated state.
FIG. 2 is a perspective breakaway view of the instant invention, illustrating the catheter as inserted with the balloons inflated.
Figures 3, 4:
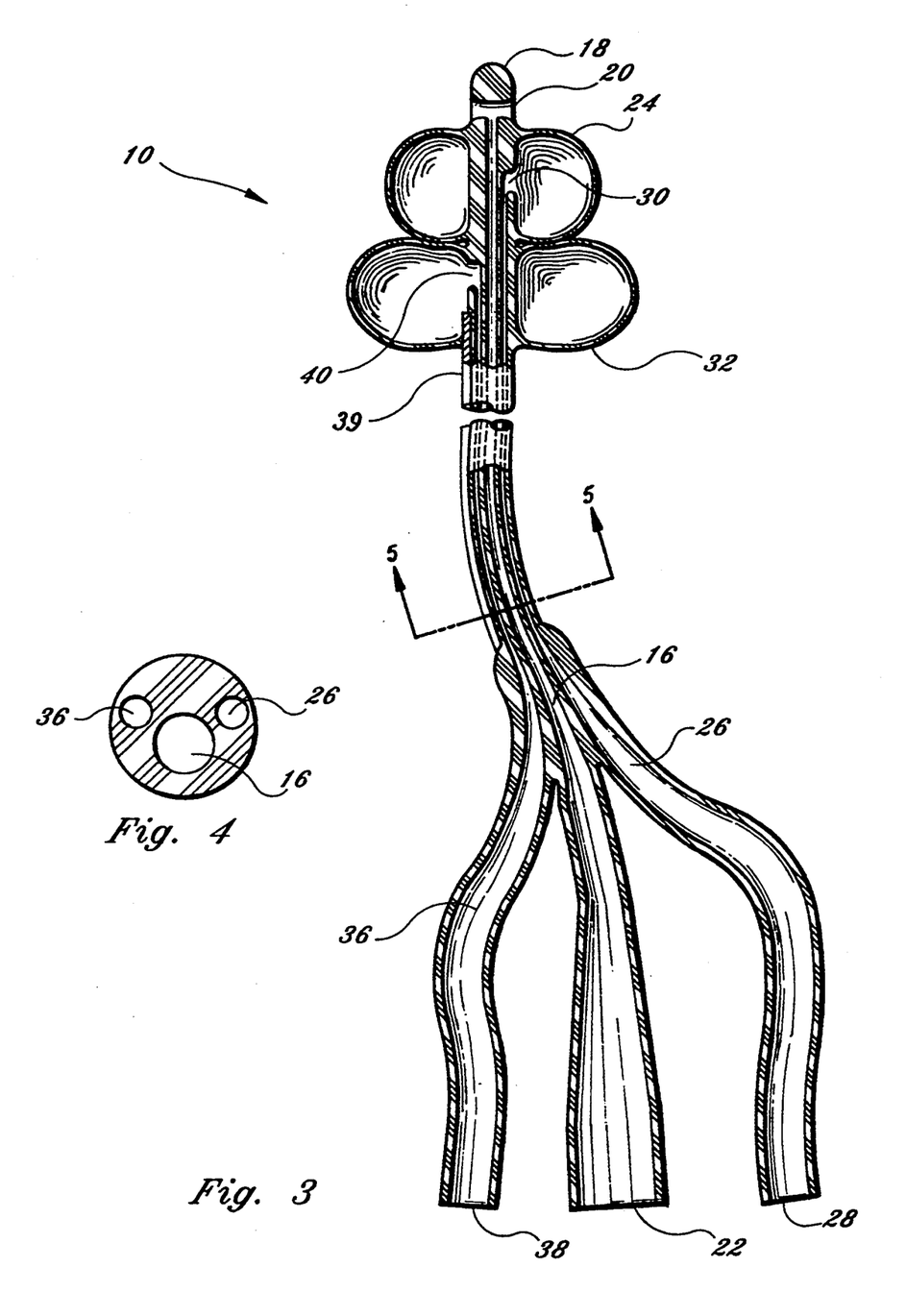
FIG. 3 is a cross sectional view of the instant invention, taken along line 3—3 of FIG. 2.
FIG. 4 is a cross sectional view of the instant invention taken along line 4—4 of FIG. 2.
Figure 5:
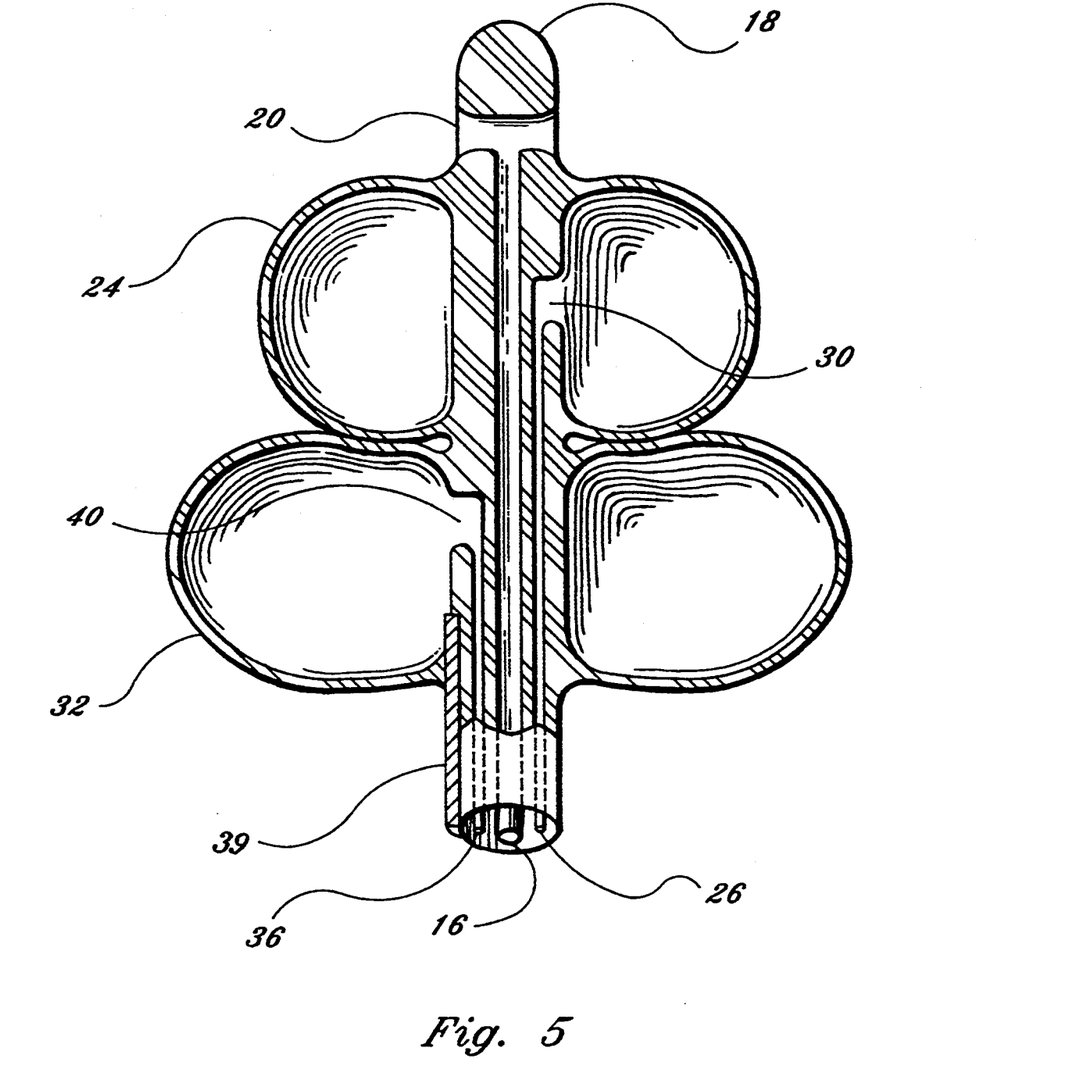
FIG. 5 is an exploded view of FIG. 3, taken along line 5—5 of FIG. 3.

FIG. 1 illustrates the no-sepsis catheter 10 depicting the trifurcating lumens 16, 26 and 36 at the distal end 14, and the drainage tip 18, the retention balloon 24 and the bacteriostasis barrier 32 at the proximal end 12. Located beneath the drainage tip 18 is a retention reservoir or balloon 24, comprising the first balloon, which when inflated secures the catheter inside the bladder 100 until fluid or air therein is discharged. The bacteriostasis barrier 32 comprises a second balloon in juxtaposition below the retention balloon 24 for preventing the ascension of bacteria into the bladder 100 by blocking the passageway created from the insertion of the catheter and by preventing the multiplication of bacteria around the internal sphincter muscle 104 entrance with a timed release pharmaceutical agent. As shown, the retention balloon 24 and the bacteriostasis barrier 32 assume the relative diametric dimensions of the catheter when deflated. The retention balloon 24 and barrier 32 are both integrally and circumferentially combined with the outer wall 11 of the catheter 10 at their peripheral ends, 24a and 24b, 32a and 32b, respectively, so that a void is formed between the outer wall 11 and each balloon. The ridges in retention balloon 24 and bacteriostasis balloon 32 illustrate their flexibility which facilitates inflation. The retention balloon is fabricated from a non-porous flexible latex, such as, synthetic rubber, polyurethane or a similar polymerized material; compositions which do not irritate tissue. The retention balloon 24 may be integrally formed with or sealing attached to the outer wall 11. Likewise, the barrier balloon 32 is fabricated from a flexible latex, however, the material employed comprises a flexible microporous membrane that facilitates diffusion by the osmosis of a bacteriostatic solution from the inside of the barrier balloon 32. The flexible membrane generally comprises permeable or semipermeable latex such as polyurethane, or other porous material capable of facilitating diffusion. The circumferential ends, 32a and 32b, of the barrier 32 are sealingly attached to or integrally combined with the outer wall 11 adjacently below the retention balloon 24, leaving a void therebetween for the receipt of the timed release bacteriostatic pharmaceutical agent, such as neosporin, recephin, bacterin, bacteriolysin or bactericidin, but not limited thereto, for killing and inhibiting bacterial growth and ascension, in combination with a tissue soothing solution, such as aloe vera. The bacteriostatic balloon 32 rests on and conforms to the bladder floor 106 proximal the internal sphincter muscle 104 when the balloon 32 is charged with the foregoing bacteriostatic fluids which treat the surrounding area.

As in the typical Foley catheter, the drainage lumen 16 has a drainage opening or inlet 20 defined by the drainage tip 18 for receiving urine stored in the bladder 100. Referencing FIG. 3, the drainage lumen 16 provides a passageway for urine to travel from the proximal end 12 to distal end 14 where it is released through drainage outlet 22, defined by lumen 16, into a drainage collection bag (not shown). The drainage bag sealingly attaches to the drainage outlet 22 to accept the fluid discharged from the patient.

FIG. 2 shows the no-sepsis catheter 10 as inserted, whereby, the drainage tip 18, retention balloon 24, and the barrier balloon 32 occupy the bladder volume 102, while the drainage lumen 16, retention lumen 26 and the barrier lumen 36 extend longitudinally through the urethra 108 and outside the body. Referencing FIGS. 3-5, the retention lumen 26 comprises tubing having a retention inlet 28 defined as an opening near the distal end 14 for fluidly communicating with retention balloon 24. Approximately 5 to 8 c.c. of water is required to fill the typical retention balloon 24 once the catheter 10 is inserted. Water is injected through the luer loc valve 28' and travels from the retention inlet 28, through the retention lumen 26, out the retention outlet 30 and into the retention balloon 24. While the post insertion load of the retention bag 24 is typically 5 to 8 c.c. of H₂O, this load may vary and still fall within the scope of the instant invention. The barrier lumen 36 provides fluid communication between barrier inlet or opening 38 and barrier outlet or opening 40 affording the charge of barrier balloon 32. Bacteriostatic fluid is injected into barrier inlet 38 and supplied to bacteriostasis barrier 32 via the barrier lumen passageway 36, where it discharges into the barrier 32 volume through barrier outlet 40. The bacteriostasis balloon 32 is typically charged with 8 to 12 c.c. of a bacteriostasis or bactericide fluid as aforementioned, having timed released characteristics accommodating approximately two (2) week recharging cycles. This allows for extended use of the no-sepsis catheter thus reducing the rate of replacement catheters, and thus the risk of introducing bacteria into the bladder. The retention inlet 28 and the barrier inlet 38 may be individually fitted with a luer loc valves 28' and 38', respectively, or similar type of valve to facilitate the injection of fluids into the respective lumens 26 and 36. To determine when the barrier balloon 32 requires recharging, an acid-base sensitive strip 39, such as variolaria lecanora, v. recella, lacmus, litmus paper, litmus coating or other similar lichens, is extended from within the barrier 32 to the distal end 12 along catheter wall 11. The acid-base sensitive strip 39 typically maintains a blue color in alkaline solution and a pink or red color in acid solution. Aloe vera is typically included in the bacteriostatic gel and diffuses with the gel onto the bladder floor 106 to sooth tissue. The aloe vera generally comprises an alkaline with a base pH to induce the acid-base sensitive strip 39 into one color as a signal that the balloon 32 is loaded. Given the acidity of urine, contact with the strip 39 causes a color change to signal time for recharging. Urine diffuses by osmosis into the barrier 32 and eventually engages the strip 39 once the balloon 32 is sufficiently depleted, signalling and allowing recharge without removal of the catheter 10.

The instant invention typically has an overall shaft diameter of 0.25 inches or less for comfortable insertion, and a standard length of twelve (12) to eighteen (18) inches. The dimensions may vary and still fall within the scope of the invention. Increased comfort is also achieved by a soft colloid surface at the proximal end 12 which engages the urethra tip.

To use the present device 10, the proximal end 12 is inserted through the urethra 108 and into the bladder 100. A drainage collection bag is attached to the drainage outlet 22. Syringes are individually coupled to the retention inlet 28 and barrier inlet 38, preferably with Luer loc valves, for inflating the retention balloon 24 and the bacteriostatic barrier 32, respectively. Once the bacteriostatic fluid is diffused from the bacteriostatic balloon 32 it may be recharged without removing the catheter 10. This placement of the catheter 10 and the recharging process are intended to be professional procedures conducive with customary medical practice.

The bacteriostatic balloon 32 lies adjacent and below retention balloon 24 allowing the retention balloon 24 to rest slightly higher above the bladder floor. In the preferred embodiment, the bacteriostatic balloon 32 conforms to the bladder floor 106 when inflated and may vary in size and shape and still meet the objectives of the instant invention. It should be noted that although the figures depict certain geometric shapes for the retention balloon 24 and the barrier balloon 32, the drawings are merely illustrative such that the balloons 24, 32 are not limited to the sizes and shapes shown.

The novel catheter disclosed herein may also include a colloid material impregnated on the exterior surface 11 of the catheter shaft as a surfactant to provide a comfortable insulation that is less irritating to the urethra when it is inserted and contained therein. The colloid material has spongy and elastic characteristics that give additional comfort while preventing sepsis and bladder spasms.

It is desirous at times to drain the maximum urine from the bladder so as to reduce bacterial growth culture in residual urine. Thus, in an alternative embodiment, the barrier balloon 32 may be designed such that it circumscribes the retention balloon 24 upon charging. This design reduces the height of the retention balloon 24 above the bladder floor 106. See FIGS. 6 and 7.

Figure 6:
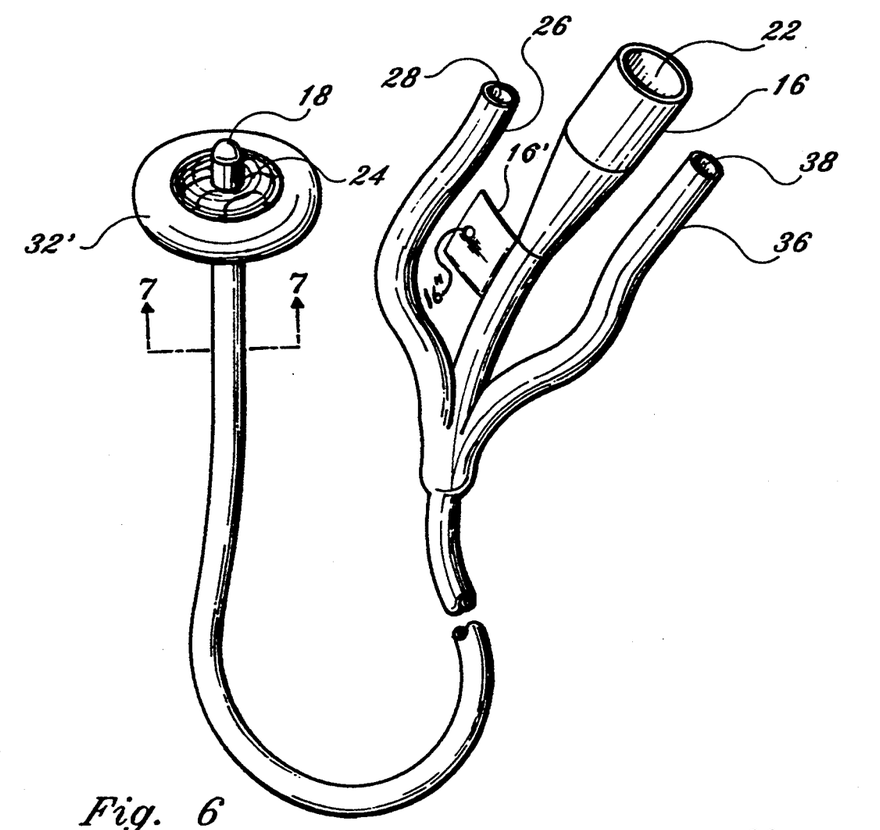
FIG. 6 is a perspective view of an alternative embodiment of the instant invention.
Figure 7:
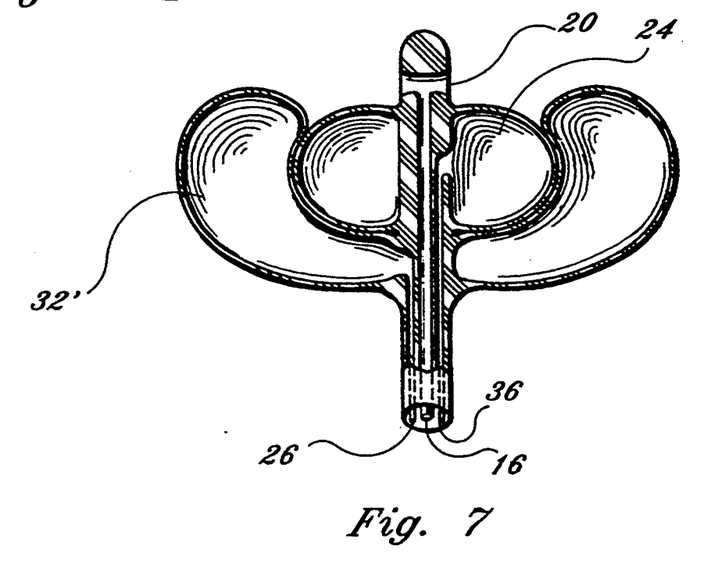
FIG. 7 is a cross sectional view of an alternative embodiment of the instant invention, taken along line 7—7 of FIG. 6.

In this alternative embodiment, as seen in FIGS. 6 and 7, the bacteriostasis barrier 32 inflates around the side of the retention balloon 24 so that the retention balloon 24 is recessed therein. In the first, or deflated state, the bacteriostasis barrier 32 is juxtaposed below the retention balloon 24 similar to the preferred embodiment as shown in FIG. 1. However, once the barrier balloon 32 is expanded into the second or inflated state by the injection of bacteriostatic fluid, it engulfs the outer edges of the retention balloon 24, unlike the original embodiment, while maintaining a narrower strip below the retention balloon 24. Consequently, the drainage tip 18 sits lower in the bladder, closer to the bladder floor, facilitating a greater volume of drainage. In contrast, the balloon 32 in the first embodiment is less conforming to the retention balloon when inflated forcing the retention balloon 24, and hence the drainage tip 18, to reside higher in the bladder. In addition, a securing tab 16' may be integrally combined with or securely attached to the drainage lumen 16 for mating with a strap strategically positioned on the patient's leg to secure, position and prevent movement of the catheter. The tab 16' may have at least one aperture 16" or button for mating with buttons or apertures, respectively, on the strap to secure the same.

The bacteriostasis barrier 32 in this alternative embodiment comprises a flexible inflatable membrane that is able to transform or expand to an inflated crescent shape. One way to effectuate this crescent shape which causes the barrier 32 to engulf the retention balloon 24 is to fabricate the barrier balloon 32 from a membrane that is more resilient than the retention balloon 24 so that the more resilient membrane expands around the less resilient membrane. Although each membrane comprises two distinct elasticity characteristics, both may be fabricated from the aforementioned materials of either synthetic rubber, latex, polyurethane, or similar material, but with varying compositions to achieve the varying degrees of elasticity. Moreover, the elasticity characteristics may be varied for the barrier 32 to adjust the height of the drainage tip inside the bladder volume as dictated by the amount of drainage that is desired. Alternatively, the bacteriostasis barrier 32 may be composed of the foregoing materials so that the barrier member 32 is more resilient at its lower or distal end 32a than at its upper or proximal end 32b. Thence, the barrier distal end 32a expands at a faster rate than the proximal end 32b upon inflation, causing the barrier 32 to surround the retention balloon 24.

Figures 8, 9, 10:
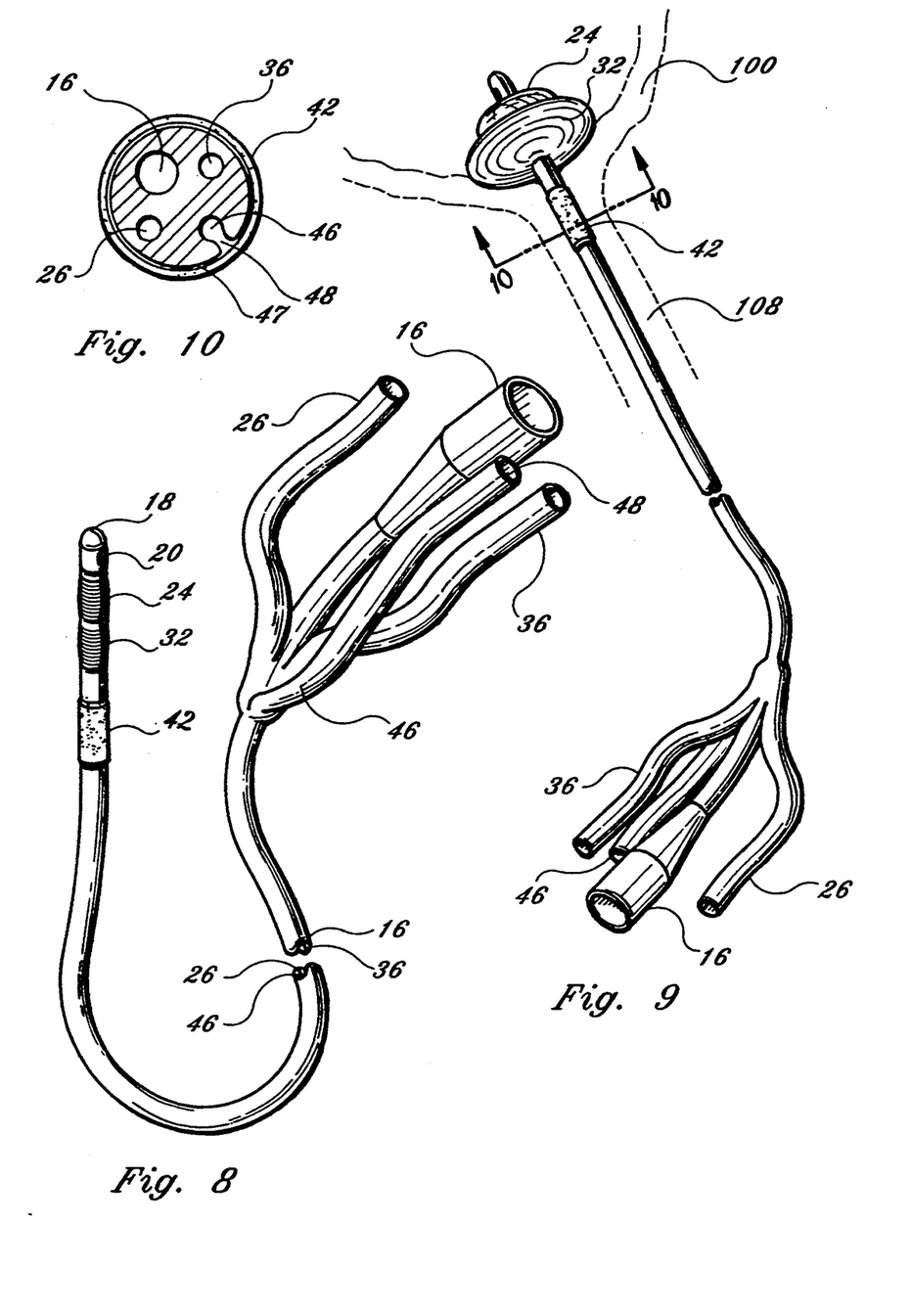
FIG. 8 is a perspective view of a second alternative of the instant invention.
FIG. 9 is a perspective view of a second alternative of the instant invention, illustrating the catheter as inserted.
FIG. 10 is a cross sectional view of the instant invention, taken along line 10—10 of FIG. 9.

In a second alternative embodiment, an exterior drug delivery member 42 is sealingly attached or integrally formed around the catheter by its peripheral ends below and apart from the barrier 32, as illustrated in FIGS. 8–10. When the catheter 10 is inserted the exterior member is disposed outside the bladder for the treatment of the urethra and the area around the exterior sphincter muscle. The exterior member 42 is a semi-permeable or permeable pliable sheet which is formed from a microporous latex for the diffusion by osmosis of a timed released antibody agent. An elongated circumferential drug delivery chamber 47 is formed between the exterior member and the catheter for storing the antibody. While the exterior member is pliable it is not typically inflated but merely expanded to contain the drug for delivery. A fourth lumen 46 is required for charging the drug delivery chamber 47. The fourth lumen 46 extends longitudinally from the distal end 14 to the proximal end 12 providing fluid communication therebetween. Drug fluid entering the fourth lumen 46 is directed through the lumen passageway, out a drug chamber aperture 48 and into the chamber 47.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A catheter for preventing the development of sepsis in patients as caused by bacteria, said catheter comprising:
   an elongated shaft having a proximal end for insertion into a patient's bladder and a distal end for pending outside the patient;
   means for draining urine from the bladder, said draining means defined by said shaft and in fluid communication with said proximal end and said distal end;
   means for the retention of said catheter in the bladder, said retention means juxtaposed below said proximal end;
   an inflatable flexible barrier balloon juxtaposed below said retention means for inflating with pharmaceutical agents when said barrier balloon is inserted inside the patient's bladder, said barrier balloon fabricated from a flexible porous material that conforms to a portion of the bladder and that allows the diffusion by osmosis of pharmaceutical agents into and around the bladder to prevent sepsis;
   said barrier balloon being substantially crescent shaped when inflated, said barrier balloon partially conforming to said retention balloon so that said means for draining urine resides low in the bladder when said barrier balloon is inflated; and
   means for inflating said barrier balloon with a pharmaceutical agent defined by said shaft.

2. A catheter according to claim 1, wherein said draining means comprises:
   a drainage lumen defined by said elongated shaft, said drainage lumen providing a passageway for fluid communication between said proximal end and said distal end;
   a drainage inlet comprising an aperture defined by said shaft at said proximal end above said retention means for receiving urine; and
   a drainage outlet comprising an opening defined by said shaft at said distal end in fluid communication with said drainage inlet for discharging urine.

3. A catheter according to claim 1, wherein said retention means comprises an inflatable retention balloon juxtaposed below said proximal end in fluid communication with said distal end.

4. A catheter according to claim 3, said retention means further comprising:
   a retention lumen defined by said shaft in fluid communication with said retention balloon; and
   a retention inlet comprising an aperture defined by said retention lumen near said distal end for providing a passageway for the injection of fluid or air to inflate said retention balloon.

5. A catheter according to claim 4, said catheter further comprising a means for attaching an injection device to said retention inlet.

6. A catheter according to claim 1, wherein said means for inflating said barrier balloon comprises:
   a barrier lumen defined by said shaft in fluid communication with said barrier balloon; and
   a barrier inlet aperture defined by said barrier lumen near said distal end, providing a passageway for the injection of a pharmaceutical agent into the balloon for inflating said balloon.

7. A catheter according to claim 1, further comprising a refill indicator means for determining when said barrier balloon requires reloading with a pharmaceutical agent.

8. A catheter according to claim 1, wherein said permeable material is a microporous latex.

9. A catheter for preventing the development of sepsis in the patient as caused by bacteria, said catheter comprising:

an elongated shaft having a proximal end for insertion into a patient's bladder and a distal end for pending outside the patient's bladder;

a drainage lumen defined by said shaft providing fluid communication between said proximal end and said distal end;

a drainage inlet comprising a drainage opening defined by said drainage lumen at said proximal end for receiving urine from the bladder;

a drainage outlet defined by said drainage lumen in fluid communication with said drainage inlet disposed at said distal end for discharging urine;

means for the retention of said catheter in the bladder, said retention means juxtaposed below said drainage inlet at said proximal end;

an inflatable flexible barrier balloon formed to said shaft for insertion inside the patient's bladder, said barrier balloon juxtaposed below said retention means for blocking the passage of bacteria from the urethra into the bladder, said barrier balloon fabricated from a flexible porous material that allows the diffusion by osmosis of a pharmaceutical agent into and around the bladder when said barrier balloon is inserted in said bladder;

means for inflating said barrier balloon with a pharmaceutical agent defined by said shaft; and a refill indicator means in communication with the contents of said barrier balloon for determining when said barrier balloon rewires reloading with a pharmaceutical agent.

10. A catheter according to claim 9, wherein said retention means comprises:

an inflatable retention balloon juxtaposed below said drainage inlet;

a retention lumen defined by said shaft in fluid communication with said retention balloon;

a retention inlet aperture defined by said retention lumen near said distal end; and a retention outlet aperture defined by said retention lumen disposed within said retention balloon, said retention outlet in fluid communication with said retention inlet, providing a passageway for the injection of fluid to inflate said retention balloon.

11. A catheter according to claim 10, wherein said retention balloon is fabricated from a non-porous expandable latex.

12. A catheter according to claim 9, wherein said means for inflating said barrier balloon comprises:

a barrier lumen defined by said shaft in fluid communication with said barrier balloon;

a barrier inlet aperture defined by said barrier lumen near said distal end; and a barrier outlet aperture defined by said barrier lumen disposed within said balloon, said barrier outlet in fluid communication with said barrier inlet as defined by said barrier lumen for providing a passageway for the injection of a pharmaceutical agent into the balloon for inflating said balloon.

13. A catheter according to claim 9, wherein said permeable material is a microporous latex.

14. A catheter according to claim 9, wherein said refill indicator means comprises a litmus strip partially disposed in said barrier balloon and disposed along said shaft.

15. A catheter for preventing the development of sepsis in patients as caused by bacteria, said catheter comprising:

an elongated shaft having a proximal end for insertion into a patient's bladder and a distal end for pending outside the patient's bladder;

a drainage lumen defined by said shaft, providing fluid communication between said proximal end and said distal end;

a drainage inlet comprising a drainage opening defined by said drainage lumen at said proximal end for receiving urine from the bladder;

a drainage outlet defined by said drainage lumen in fluid communication with said drainage inlet disposed near said distal end for discharging urine;

an inflatable retention balloon juxtaposed below said drainage inlet;

a retention lumen defined by said shaft in fluid communication with said retention balloon;

a retention inlet aperture defined by said retention lumen near said distal end;

a retention outlet aperture defined by said retention lumen disposed in said retention balloon, said retention lumen providing fluid communication between said retention inlet and said retention outlet for providing a passageway for the injection of fluid for inflating said retention balloon;

said retention balloon fabricated from a non-porous, expandable latex;

an inflatable barrier balloon juxtaposed below said retention balloon, said barrier balloon fabricated from a permeable material for the diffusion by osmosis of a pharmaceutical agent;

a barrier lumen defined by said shaft in fluid communication with said barrier balloon;

a barrier inlet aperture defined by said barrier lumen near said distal end;

a barrier outlet aperture defined by said lumen within said barrier balloon such that said barrier lumen provides fluid communication between said barrier inlet and said barrier outlet for the injection of a pharmaceutical agent into the barrier balloon to inflate said barrier balloon; and a litmus coating disposed longitudinally along said shaft from said barrier balloon to said distal end for determining when said barrier balloon requires reloading of a pharmaceutical agent, wherein said litmus coating changes color upon contact with urine from the bladder.

16. A catheter according to claim 15, further comprising:

a microporous membrane disposed below said barrier balloon, wherein said microporous membrane remains outside the bladder when said catheter is inserted;

a drug delivery chamber defined by a void between said member and said catheter for storing a drug to be delivered;

a drug delivery lumen defined by said shaft in fluid communication with said drug delivery chamber; and a drug delivery aperture defined by said drug delivery lumen near said distal end for injecting said drug chamber with an antibody for treating the area outside the bladder with an antibody by diffusion through said porous membrane.

17. A catheter according to claim 15, further comprising:

a water pre-filled syringe in fluid communication with said retention inlet for inflating said retention balloon with water after placement of said catheter in the bladder; and a pharmaceutical agent pre-filled syringe in fluid communication with said barrier inlet for inflating said barrier balloon with the agent after placement of said catheter in the bladder.

18. A catheter according to claim 15, further including:

a securing tab depending from said drainage lumen for securing said catheter to a strap worn on a patient's leg; and a means for securing said tab to the strap to hold said catheter in place.

* * * * *